United States Patent
Duchamp

(10) Patent No.: US 7,115,137 B2
(45) Date of Patent: Oct. 3, 2006

(54) BALLOON CATHETER HAVING A BALLOON DISTAL SKIRT SECTION WITH A REDUCED OUTER DIAMETER SECURED TO A SOFT DISTAL TIP MEMBER

(75) Inventor: Jacky G. Duchamp, Campbell, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 488 days.

(21) Appl. No.: 10/304,598

(22) Filed: Nov. 26, 2002

(65) Prior Publication Data

US 2003/0114794 A1    Jun. 19, 2003

Related U.S. Application Data

(63) Continuation-in-part of application No. 09/735,692, filed on Dec. 12, 2000, now Pat. No. 6,488,654.

(51) Int. Cl.
*A61M 29/04* (2006.01)
*A61M 25/10* (2006.01)

(52) U.S. Cl. ..................... 606/194; 604/103

(58) Field of Classification Search ................ 604/103.05–103.07, 103, 96.01; 606/194
See application file for complete search history.

(56) References Cited

U.S. PATENT DOCUMENTS

| | | | |
|---|---|---|---|
| 3,694,280 A | 9/1972 | Hoef | |
| 4,321,226 A | 3/1982 | Markling | |
| 4,384,942 A | 5/1983 | Glowacki | |
| 4,782,834 A * | 11/1988 | Maguire et al. | 606/194 |
| 4,921,483 A * | 5/1990 | Wijay et al. | 604/103.1 |
| 5,042,985 A * | 8/1991 | Elliott et al. | 606/192 |
| 5,114,423 A * | 5/1992 | Kasprzyk et al. | 606/27 |
| 5,215,614 A | 6/1993 | Wijkamp et al. | |
| 5,290,230 A * | 3/1994 | Ainsworth et al. | 604/103.09 |
| 5,409,495 A * | 4/1995 | Osborn | 623/1.11 |
| 5,425,712 A | 6/1995 | Goodin | |
| 5,525,388 A | 6/1996 | Wand et al. | |
| 5,533,968 A | 7/1996 | Muni et al. | |
| 5,827,225 A | 10/1998 | Ma Schwab | |
| 5,980,530 A * | 11/1999 | Willard et al. | 623/1.11 |
| 6,024,752 A * | 2/2000 | Horn et al. | 606/192 |
| 6,165,152 A | 12/2000 | Becker et al. | |
| 6,206,852 B1 | 3/2001 | Lee | |
| 6,264,683 B1 * | 7/2001 | Stack et al. | 623/1.11 |
| 6,368,301 B1 * | 4/2002 | Hamilton et al. | 604/103 |
| 6,575,934 B1 | 6/2003 | Duchamp | |
| 6,692,461 B1 | 2/2004 | Wantink | |
| 6,723,113 B1 * | 4/2004 | Shkolnik | 606/194 |

(Continued)

*Primary Examiner*—Anhtuan T. Nguyen
*Assistant Examiner*—Elizabeth Houston
(74) *Attorney, Agent, or Firm*—Fulwider Patton LLP

(57) ABSTRACT

A catheter having an elongated shaft, an inflatable balloon on a distal shaft section, and a distal tip member bonded to a surface of the distal end of the balloon. The balloon has a proximal skirt section and a distal skirt section sealingly secured to the shaft, and an inflatable section therebetween with an interior in fluid communication with the at least one lumen of the shaft. The distal skirt section of the balloon has a proximal portion, and a distal portion with a smaller outer diameter than the proximal portion. Preferably, the distal tip member has a proximal section with an inner surface bonded to an outer surface of the distal portion of the distal skirt section, and a distal section extending beyond the distal end of the balloon.

14 Claims, 1 Drawing Sheet

U.S. PATENT DOCUMENTS

2002/0082549 A1* 6/2002 Duchamp ................ 604/96.01
2003/0078613 A1* 4/2003 Heidner ..................... 606/194
2004/0015183 A1* 1/2004 Lim et al. .................. 606/194

* cited by examiner

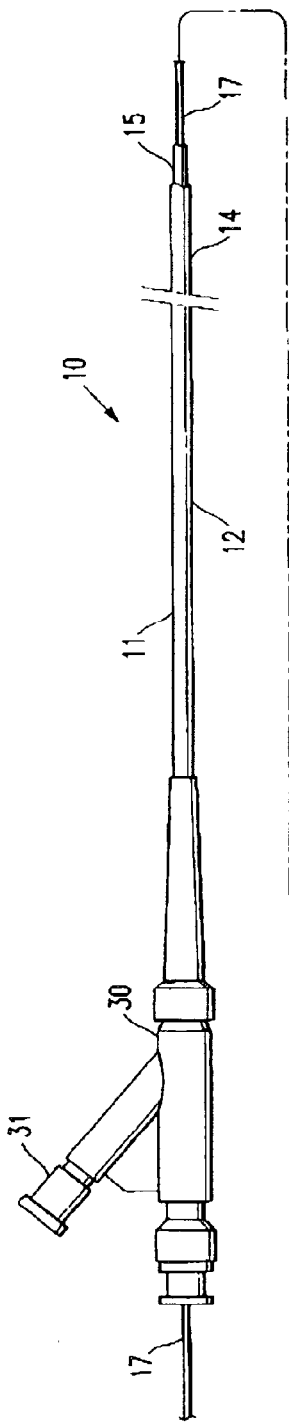
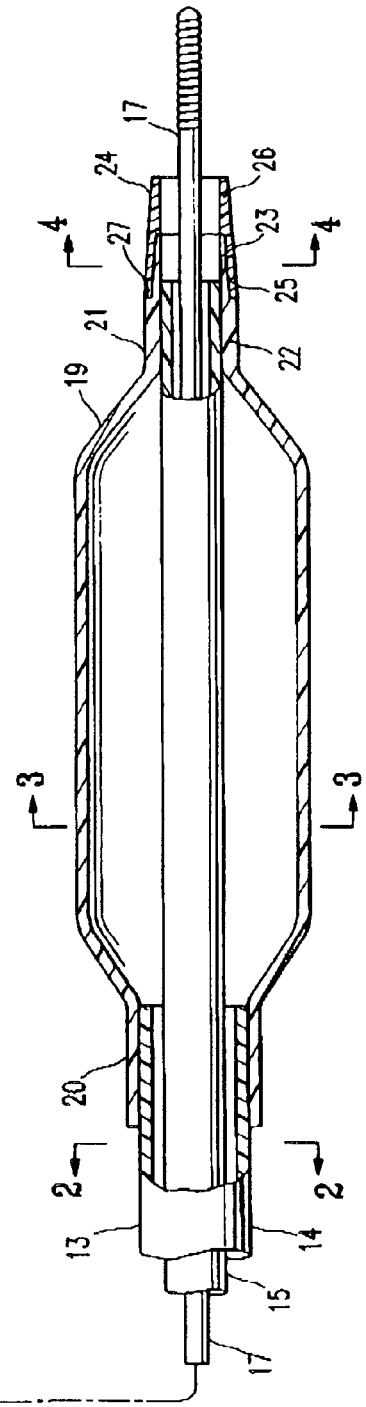
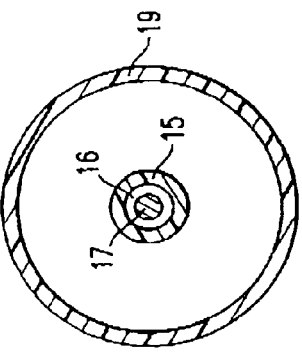
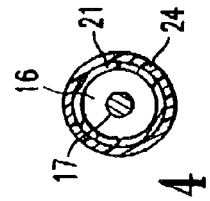
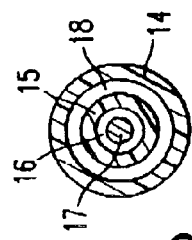

BALLOON CATHETER HAVING A BALLOON DISTAL SKIRT SECTION WITH A REDUCED OUTER DIAMETER SECURED TO A SOFT DISTAL TIP MEMBER

CROSS REFERENCE TO RELATED APPLICATIONS

This Application is a continuation-in-part of U.S. application Ser. No. 09/735,692, filed on Dec. 12, 2000, now U.S. Pat. No. 6,488,654.

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

An essential step in effectively performing a PTCA procedure is properly positioning the balloon catheter at a desired location within the coronary artery. To properly position the balloon at the stenosed region, the catheter shaft must be able to transmit force along the length of the catheter shaft to allow it to be pushed through the vasculature. However, the catheter shaft must also retain sufficient flexibility to allow it to track over a guidewire through the often tortuous vasculature. Additionally, the catheter also must have good crossability (i.e., the ability of the catheter distal end to cross stenosed portions of the vascular anatomy).

Conventional intravascular catheters have commonly included a soft distal tip to prevent or minimize injury to the vessel during advancement of the catheter therein. One difficulty has been forming a connection between the soft tip and the catheter which is sufficiently strong to prevent disengagement of the soft tip or kinking at the junction between the soft tip and catheter shaft. Additionally, it is necessary to balance the strength of the connection between the soft tip and the catheter shaft with the need to minimize the stiffness of the distal end of the catheter. Minimizing the stiffness of the distal end of the catheter results in improved maneuverability of the catheter.

Accordingly, it would be a significant advance to provide a catheter with a soft tip having improved performance. This invention satisfies these and other needs.

SUMMARY OF THE INVENTION

The invention is directed to a catheter having an elongated shaft with at least one lumen, an inflatable balloon on a distal shaft section, and a distal tip member bonded to the distal end of the balloon. The balloon has a proximal skirt section and a distal skirt section sealingly secured to the shaft, and an inflatable section therebetween with an interior in fluid communication with the at least one lumen of the shaft. The distal skirt section of the balloon has a proximal portion, and a distal portion with a smaller outer diameter and/or a smaller wall thickness than the proximal portion. Preferably, the distal tip member has a proximal section with an inner surface bonded to an outer surface of the distal portion of the balloon distal skirt section, and a distal section extending beyond the distal end of the balloon. The distal tip configuration provides a flexible distal end with a high strength, secure attachment between the distal tip member and the balloon, facilitating advancing and positioning the catheter in a patient's body lumen.

A balloon catheter of the invention generally comprises an elongated shaft having a proximal end, a distal end, and at least one lumen, and an inflatable balloon on the distal shaft section with an interior in fluid communication with the at least one lumen. More specifically, the shaft typically has an inflation lumen (i.e., the at least one lumen of the shaft) which is in fluid communication with the balloon interior and which extends within proximal and distal shaft sections, and a guidewire receiving lumen extending at least within the distal shaft section. In a presently preferred embodiment, the shaft comprises an outer tubular member defining the inflation lumen, and an inner tubular member defining at least a portion of the guidewire receiving lumen. However, a variety of suitable shaft designs may be used including dual-lumen type shafts. The balloon distal skirt section has an inner surface bonded, for example fusion or adhesive bonded, to an underlying portion of the shaft (e.g., the inner tubular member), and an outer surface bonded to the distal tip member. In a presently preferred embodiment, the distal tip member has at least a portion distal to the inner tubular member, and defines a distal portion of the guidewire lumen in fluid communication with the portion of the guidewire lumen defined by the inner tubular member. The balloon catheter of the invention may comprise a variety of suitable balloon catheters, including coronary and peripheral dilatation catheters, stent delivery catheters, drug delivery catheters, and the like.

In a presently preferred embodiment, the balloon distal skirt section has an outer diameter which abruptly decreases from the proximal to the distal portions of the distal skirt section, so that the distal skirt section has a step transition forming a shoulder between the proximal and the distal sections of the distal skirt section. However, the distal skirt section may have a variety of suitable configurations, including a more gradual, tapered transition from the proximal to the distal portion thereof. The distal portion of the distal skirt section has an outer diameter which is typically about 5% to about 25%, more preferably about 10% to about 15% less than the outer diameter of the proximal portion of the distal skirt section before heat bonding to the tip member. The distal portion typically thins somewhat during heat bonding to the tip member, so that the difference between the size of the proximal and distal portions may increase by another 5% to 10% as a result of the bonding process. In one embodiment, the wall thickness of the distal skirt section distal portion is about 10% to about 50% less than the wall thickness of the proximal portion of the distal skirt section before heat bonding to the tip member.

Preferably, the distal tip member has a proximal end which abuts the shoulder (or other transition configuration) in the outer surface of the distal skirt section, which facilitates proper positioning of the distal tip member during assembly of the catheter. The distal tip member is bonded to the reduced diameter distal portion of the distal skirt section, as for example by heat fusion or adhesive bonding. The polymeric material of the distal tip member typically flows during fusion bonding, so that the outer surface of the distal tip typically has a distally tapering outer diameter.

The distal tip member is typically softer and more flexible than the section of the shaft proximally adjacent thereto (e.g., the inner tubular member), and the balloon. The distal tip member may be formed of a different material or the same material as the balloon, but is preferably compatible with the polymeric material of the balloon to facilitate fusion bonding thereto. Preferably, the distal tip member is formed of a material having a lower Shore durometer hardness than the polymeric material forming at least part of the inner tubular member and the polymeric material of the balloon, to provide a soft, flexible, atraumatic distal end, which consequently provides improved catheter maneuverability and decreases the risk of damage to the patient's vessel during advancement of the catheter therein. The Shore durometer hardness of the polymeric material forming the distal tip member is typically about 40D to about 82D, preferably about 65D to about 75D. In a presently preferred embodiment, the distal tip member is formed of a polyurethane including polyurethane copolymers such as PELLETHANE (a polyester polyurethane copolymer), available from Dow Plastics, or a polyamide including polyether block amide copolymers such as PEBAX, available from Autochem. However, the distal tip member may be formed of a variety of suitable materials such as polyolefin based copolymers, including polyethylene based adhesive polymers such as an ethylene-acrylic acid copolymer (e.g., PRIMACOR available from Dow Chemical Co.).

A catheter of the invention has excellent maneuverability and crossability due to the distal end of the catheter having the distal tip member secured to the reduced outer diameter section of the distal skirt section of the balloon. The distal tip configuration provides decreasing flexibility at the catheter distal end, for improved handling and performance, and excellent tensile strength at the distal tip attachment without disadvantageously increasing the stiffness or profile of the distal end of the catheter. These and other advantages of the invention will become more apparent from the following detailed description and exemplary drawings.

BRIEF DESCRIPTION OF THE DRAWINGS

FIG. 1 is an elevational view, partially in section, of a balloon catheter which embodies features of the invention.

FIG. 2 is a transverse cross sectional view of the catheter shown in FIG. 1, taken along line 2—2.

FIG. 3 is a transverse cross sectional view of the catheter shown in FIG. 1, taken along line 3—3.

FIG. 4 is a transverse cross sectional view of the catheter shown in FIG. 1, taken along line 4—4.

DETAILED DESCRIPTION OF THE INVENTION

FIG. 1 illustrates an over-the-wire balloon catheter 10 embodying features of the invention. Catheter 10 generally comprises an elongated catheter shaft 11 having a proximal end, a distal end, a proximal shaft section 12, a distal shaft section 13, an outer tubular member 14, and an inner tubular member 15. Inner tubular member 15 defines a guidewire lumen 16 adapted to slidingly receive a guidewire 17, and the coaxial relationship between outer tubular member 14 and inner tubular member 15 defines annular inflation lumen 18, as best shown in FIG. 2, illustrating a transverse cross section of the catheter of FIG. 1, taken along line 2—2. An inflatable balloon 19 is disposed on the distal shaft section 13, having a proximal skirt section 20 sealingly secured to the distal end of outer tubular member 14, and a distal skirt section 21 sealingly secured to the distal end of inner tubular member 15, so that its interior is in fluid communication with inflation lumen 18. An adapter 30 at the proximal end of the shaft is configured to provide access to guidewire lumen 16, and to direct inflation fluid through arm 31 into inflation lumen 18. FIG. 1 illustrates the balloon 19 inflated, with a central working length section, and proximal and distal tapered sections at either end of the working length section between the working length section and the proximal and distal skirt sections 20, 21, respectively. The distal end of the catheter may be advanced to a desired region of a patient's body lumen in a conventional manner, and balloon 19 inflated to perform a procedure such as dilating a stenosis or expanding a stent (not shown), the balloon deflated, and the catheter repositioned or withdrawn from the body lumen. FIG. 3 illustrates a transverse cross section of the catheter of FIG. 1, taken along line 3—3.

The distal skirt section 21 of the balloon 19 has a proximal portion 22 and a distal portion 23. The distal portion 23 has a smaller outer diameter and wall thickness than the proximal portion 22. In the embodiment of FIG. 1, a step transition forms a shoulder 27 in the outer surface of the distal skirt section 21. A distal tip member 24 forming the distal end of the catheter has a proximal section 25 with an inner surface bonded to the outer surface of the distal portion 23 of the balloon distal skirt section 21. The distal tip member 24 has a distal section 26 extending distally beyond the distal end of the distal skirt section 21, to define a distal portion of the guidewire lumen 16 and a guidewire distal port in the distal end of the catheter. In the embodiment of FIG. 1, the distal skirt section 21 defines a portion of the guidewire lumen 16 proximal to the distal portion of the guidewire lumen 16 defined by the distal tip member 14. In one embodiment, the proximal portion 22 of the distal skirt section 21 has an outer diameter of about 0.65 to about 1 mm, and the distal portion 23 has an outer diameter of about 0.6 to about 0.8 mm. The distal tip member 24 typically has a length of about 1.5 to about 3 mm, and the distal skirt section 21 has a length of about 1.5 to about 3 mm. The distal portion 23 of the distal skirt section 21 is typically about 25% to about 65% of the length of the distal skirt section 21.

The distal skirt section 21 of the balloon 19 is bonded, preferably by fusion bonding, to the shaft inner tubular member 15 and distal tip member 24. In the embodiment of FIG. 1, the distal end of the inner tubular member 15 is located distal to the proximal portion 22 of the distal skirt section 21 of the balloon 19 and proximal to the distal end of the distal skirt section 21, so that the distal portion 23 of the distal skirt section 21 surrounds a distal end of the inner tubular member 15. However, the distal end of the inner tubular member may have a variety of suitable locations, including radially aligned with the proximal end of the distal portion 23 or proximal thereto. In the embodiment of FIG. 1, the distal skirt section 21 has a uniform inner diameter from the proximal to the distal portions 22, 23 of the distal skirt section 21, and the distal tip member 24 distal portion 26 has an inner diameter about equal to the inner diameter of the distal skirt section 21 (i.e., equal within normal manufacturing tolerances).

In a method of making a balloon catheter of the invention, the reduced outer diameter of the distal portion 23 of the balloon distal skirt section 21 is preferably formed by removing polymeric material from the outer surface of the distal skirt section 21. In one embodiment in which the balloon 19 is formed by blow molding, the material is preferably removed after the balloon is blow molded. The material is preferably mechanically removed as for example with a lathe, although a variety of suitable methods may be used including using a laser or otherwise cutting or removing the material. The cutting or abrading tool of the lathe removes material from around the entire circumference of the distal skirt section 21 to reduce the wall thickness thereof and form the distal portion 23 of the distal skirt section 21. The reduced diameter distal portion 23 typically has a uniform outer diameter along the length thereof before being fusion bonded to the distal tip member 24, and a tapering outer diameter after bonding. Specifically, the distal tip member 24 is positioned on the reduced diameter distal skirt section 21, with the proximal end of the distal tip member 24 abutting the shoulder 27 in the outer surface of the distal skirt section 21. The polymeric materials are heated, as for example using a laser or induction heating, and typically with heat shrink tubing therearound, to fusion bond the tip member 24 to the distal skirt section 21. During fusion bonding, the polymeric materials typically melt or soften, and flow. As a result, the outer surface of the reduced diameter distal portion 23 and the distal tip member 24 typically become tapered distally to a smaller outer diameter along the length thereof. Preferably, the distal skirt section 21 is caused to also bond to the inner tubular member 15 during bonding to the distal tip member 24. Thus, with a mandrel (not shown) in the guidewire lumen 16 to keep the lumen open, heat is directed at a location on the proximal portion 22 of the distal skirt section 21 and distally thereof to the distal end of the distal tip member 24 to bond the distal skirt section 21 to the outer surface of the inner tubular member 15 and to the inner surface of the distal tip member 24. In one embodiment, the bond between the distal skirt section 21 and the inner tubular member 15 has a proximal end spaced distally apart from the distal end of the distal tapered section of the inflated balloon 19. The bond between the distal skirt section 21 and the inner tubular member 15 typically has a length of about 15% to about 35% of the length of the balloon distal skirt section 21. Although not illustrated, the length of the proximal portion 22 of the distal skirt section fusion bonded to the inner tubular member typically has an outer surface tapering distally, similar to the outer surface of the distal tip member 24 illustrated in FIG. 1.

To the extent not previously discussed herein, the various catheter components may be formed and joined by conventional materials and methods. For example, inner tubular member 15 can be formed by conventional techniques, such as by extruding and necking materials found useful in intravascular catheters such a polyethylene, polyvinyl chloride, polyesters, polyamides, polyimides, polyurethanes, and composite materials, and is preferably a multilayered tubular member. Additionally, although not illustrated, coiled or braided reinforcements may be included in the shaft at various locations, as is conventionally known. The balloon 19 can be formed of a variety of suitable polymeric materials, and is preferably compatible with the polymeric material of the distal tip member 24 to facilitate fusion bonding thereto. In one embodiment, the distal tip member 24 is formed of the same type of material as the balloon (i.e., a polyamide) but having a lower Shore durometer hardness than the polymeric material of the balloon. In one embodiment, the distal tip member 24 is formed of a blend of PEBAX 55D and PEBAX 63D polymers.

The length of the dilatation catheter 10 is generally about 108 to about 200 centimeters, preferably about 137 to about 145 centimeters, and typically about 143 centimeters for PTCA. The outer tubular member 14 distal section has an outer diameter (OD) of about 0.028 to about 0.036 inch (0.70–0.91 mm), and an inner diameter (ID) of about 0.024 to about 0.035 inch (0.60–0.89 mm), and the outer tubular member 14 proximal section has an OD of about 0.036 to about 0.043 inch (0.91–1.1 mm), and an inner diameter (ID) of about 0.032 to about 0.036 inch (0.81–0.91 mm). The inner tubular member 15 has an OD of about 0.017 to about 0.026 inch (0.43–0.66 mm), and an ID of about 0.015 to about 0.019 inch (0.38–0.48 mm) depending on the diameter of the guidewire to be used with the catheter. The balloon 19 has a length of about 8 mm to about 40 mm, and an inflated working diameter of about 1.5 mm to about 5 mm.

While the present invention has been described herein in terms of certain preferred embodiments, those skilled in the art will recognize that modifications and improvements may be made without departing form the scope of the invention. For example, although primarily discussed in terms of an embodiment in which the distal portion 23 of the distal skirt section 21 has a reduced outer diameter and wall thickness with the distal tip member bonded to the outer surface thereof, the distal portion 23 could alternatively have material removed from the inner surface thereof, so that the distal tip member is bonded to the inner surface of the distal skirt section 21. Additionally, although the catheter 10 illustrated in the figures is an over-the-wire balloon catheter, the catheter of the invention may be a variety of suitable balloon catheters, including rapid exchange type balloon catheters having a guidewire proximal port located distal to the proximal end of the shaft, a guidewire distal port in the distal end of the shaft, and a relatively short guidewire lumen extending therebetween. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated shaft having a proximal end, a distal end, and at least one lumen;
   b) an inflatable balloon on a distal shaft section, having a proximal skirt section and a distal skirt section sealingly secured to the shaft, and an inflatable section therebetween with an interior in fluid communication with the at least one lumen of the shaft, the distal skirt section having a proximal portion at least in part bonded to the shaft, a distal portion with a smaller outer diameter than the proximal portion of the distal skirt section, and a uniform inner diameter from the proximal to the distal portion thereof; and
   c) a distal tip member having a proximal end, an outer diameter not greater than the outer diameter of the proximal portion of the distal skirt section of the balloon, a proximal section with an inner surface bonded to an outer surface of the distal portion of the distal skirt section such that the proximal end of the distal tip member is distal to the bonded proximal portion of the distal skirt section, and a distal section extending beyond a distal end of the balloon.

2. The catheter of claim 1 wherein the distal skirt section of the balloon has a step transition between the proximal and distal portions forming a shoulder in the outer surface of the distal skirt section.

3. The catheter of claim 2 wherein the outer diameter of the distal portion of the distal skirt section is about 10% to about 35% less than the outer diameter of the proximal portion.

4. The catheter of claim 1 wherein the distal portion of the distal skirt section has a wall thickness less than a wall thickness of the proximal portion.

5. The catheter of claim 4 wherein the wall thickness of the distal portion of the distal skirt section is about 15% to about 60% less than the wall thickness of the proximal portion.

6. The catheter of claim 2 wherein the distal tip member has a proximal end abutting the shoulder of distal skirt section.

7. The catheter of claim 1 wherein the distal tip member distal section has an inner diameter about equal to the inner diameter of the distal portion of the distal skirt section.

8. The catheter of claim 1 wherein the at least one lumen of the shaft is an inflation lumen, and the shaft comprises an outer tubular member defining the inflation lumen, and an inner tubular member defining at least a portion of a guidewire lumen.

9. The catheter of claim 8 wherein the distal tip member defines a distal portion of the guidewire lumen in fluid communication with the portion of the guidewire lumen defined by the inner tubular member.

10. The catheter of claim 9 wherein the distal skirt section defines a portion of the guidewire lumen proximal to the distal portion of the guidewire lumen defined by the distal tip member.

11. The catheter of claim 9 wherein the distal portion of the distal skirt section has an inner surface bonded to an outer surface of the inner tubular member.

12. The catheter of claim 1 wherein the distal tip member proximal section is fusion bonded to the distal skirt section.

13. The catheter of claim 1 wherein the outer surface of the distal tip member tapers distally from the proximal to the distal end thereof.

14. A balloon catheter, comprising:
   a) an elongated shaft having a proximal end, a distal end, an inflation lumen, and a guidewire lumen, and the shaft comprises an outer tubular member defining the inflation lumen, and an inner tubular member defining at least a portion of the guidewire lumen;
   b) an inflatable balloon on a distal shaft section, having a proximal skirt section sealingly secured to the shaft, a distal skirt section sealingly secured to the shaft and extending distally thereof to define a portion of the guidewire lumen, and an inflatable section therebetween with an interior in fluid communication with the at least one lumen of the shaft, the distal skirt section having a proximal portion at least in part bonded to the shaft, and a distal portion with a smaller outer diameter than the proximal portion of the distal skirt section; and
   c) a distal tip member having a proximal end, a proximal section with an inner surface bonded to an outer surface of the distal portion of the distal skirt section such that the proximal end of the distal tip member is distal to the bonded proximal portion of the distal skirt section, and a distal section extending beyond a distal end of the balloon such that the distal tip member defines a distal portion of the guidewire lumen distal to the portion of the guidewire lumen defined by the distal skirt section.

* * * * *